United States Patent [19]

Empey et al.

[11] 4,070,535
[45] * Jan. 24, 1978

[54] CELLULASE-FREE XANTHAN GUM AND PROCESS FOR PRODUCING SAME

[75] Inventors: Richard A. Empey, San Diego; David J. Pettitt, Powai, both of Calif.

[73] Assignee: Merck & Co., Inc., Rahway, N.J.

[*] Notice: The portion of the term of this patent subsequent to Nov. 11, 1992, has been disclaimed.

[21] Appl. No.: 606,899

[22] Filed: Aug. 22, 1975

[51] Int. Cl.$^2$ ............................................. C08B 37/00
[52] U.S. Cl. ................................................... 536/114
[58] Field of Search ....................... 260/209 R, 234 R; 536/114, 120

[56] References Cited

U.S. PATENT DOCUMENTS

| | | | |
|---|---|---|---|
| 3,256,271 | 6/1966 | Schweiger | 260/234 R |
| 3,349,077 | 10/1967 | Schweiger | 260/209 R |
| 3,531,465 | 8/1968 | Bridgeford | 260/209 R |
| 3,865,806 | 2/1975 | Knodel | 260/209 R |
| 3,919,189 | 11/1975 | Empey et al. | 536/114 |

Primary Examiner—Johnnie R. Brown
Attorney, Agent, or Firm—Donald J. Perrella

[57] ABSTRACT

Intimate intermingling, as in a tumble reactor, of wet particulate xanthan gum, with either propylene oxide, β-propiolactone, glutaraldehyde or pivalolactone, as essentially the only gas present, at about 40°–70° C., for from 1–5 hours, produces xanthan gum in which the cellulase enzyme is inactivated, but in which the viscosity of solutions is increased; the propylene oxide is removed to afford a residual propylene oxide content of not more than 300 ppm in the product xanthan gum.

9 Claims, No Drawings

CELLULASE-FREE XANTHAN GUM AND PROCESS FOR PRODUCING SAME

SUMMARY OF THE INVENTION

The process of this invention for inactivating cellulase enzyme in xanthan gum consists essentially of: intmately intermingling wet xanthan gum, preferably in coarse particulate form, and either propylene oxide gas or gaseous glutaraldehyde, B-propiolactone or pivalolactone, as essentially the only gas present in the intermingling zone. The intermingling is carried out at a temperature between about 40° and about 70° C., for from about 1 to about 5 hours.

The starting material is xanthan gum, a hydrophilic colloid prepared by bacteria of the genus Xanthomonas. Its preparation and properties are described in numerous publications and patents.

Xanthan gum has been reacted or treated with alkyl oxides in the past. Propylene oxide is a known sterilizing agent, see U.S. Pat. No. 3,206,275. In addition, propylene oxide derivatives have been made of xanthan gum, (see U.S Pat. Nos. 3,349,077 and 3,256,271); and propylene oxide has been used to reduce bacterial contamination (see U.S. Pat. No. 3,919,189). However, these processes have all been concerned with the reaction or treatment of dry xanthan gum with propylene oxide. Most products are either grainy or insoluble, and therefore do not possess the desired rheological properties of xanthan gum. We have now found, that an unexpected cellulase-inactivation effect occurs when the xanthan gum is used as a wet particulate material.

By the term "wet particulate xanthan gum" is meant xanthan gum which has been totally precipitated from its fermentation broth, washed, and recovered as a "press cake"; the latter is coarsely comminuted and used in the process of this invention. A factor important in this invention is the adjustment of the pH of the beer containing the xanthan gum prior to precipitation. Generally, the beer should be adjusted to a pH of between from about 4 to about 8 for best results during the subsequent inactivation process. The particle size of wet xanthan gum is not critical to the operation of the invention, as long as fairly small particles are used. generally, the press cake contains about 50–60% xanthan gum solids, about 10–20% alcohol (left from the precipitation step) and 20–25% water. The total analysis of the press cake totals 100%. The cake is broken up into particles, and added to the chosen apparatus to be mixed with the propylene oxide.

It is noted here that other oxides, in addition to those listed as preferable can be used to deactivate the cellulase enzyme. These include glycidol, epichlorohydrin, ethylene oxide, and others.

The process conditions utilize about a 2–20% (based on the dry weight of the xanthan gum) concentration level of chosen alkyl oxide or lactone, preferably 4–12% by weight. Hereafter the term "oxide" will be used to refer to all four of the preferred reagents.

As noted the temperature range of the inactivation can be from about 40° to about 70° C., and a reaction time is usually from about 1to about 5 hours. Time of reaction depends on oxide level and temperature. The higher for each, the faster the reaction proceeds. For example, about 1 hour at about 70° C. is adequate using 5–10% propylene oxide. Where the temperature is dropped to about 50° C., te reaction time is about 4 hours. Optimum conditions are in the range of from about 8 to about 12% of the chosen oxide, and between about 1 hour at about 70° C., or about 4 hours at at 50° C.

Following the end of the reaction, the reactor is flushed with an inert gas to remove the oxide and to obtain the cellulase inactivated xanthan gum having a level of residual oxide of below 300 ppm in the gum, and preferably below 180 ppm.

The process is one of "intimate intermingling", referring to a dynamic procedure which continually exposes gum surfaces to the oxide gas. Such a dynamic situation can be obtained in batch closed reactors which tumble the particulate solid inside the reactor providing a cascade contact of the solids and the oxide — these are particularly suitable when the oxide usage moisture content of the gum is desired to be kept in the low usages set out above.

Another type of suitable reactor is a vertical conduit provided with baffling to cause the solids to cascade through the upflowing propylene oxide. Still another reactor is a fluid bed vessel with the particulate gum being fluidized by the upflowing propylene oxide gas.

The oxide may be removed by any physical procedure which does not contaminate the gum, such as, evacuation of the reactor; stripping with aseptic inert gas such as nitrogen.

The advantage of this process and the product so produced, over that of the prior art lies in the properties of the final xanthan gum: it remains soluble and can be used in place of xanthan gum, while it can be blended with cellulosic resins and gums. The cellulase-inactivated xanthan gum can also be handled in the same physical location with cellulase derivatives without the hazard of contamination of an entire production plant with enzyme. In addition, the xanthan gum produces a higher viscosity in solutions, a highly desirable improvement in the product.

We have also found that there is no inactivation of cellulase enzyme when dry xanthan gum, or xanthan gum having solids content above about 90% is used. The entire inventive reaction, in fact, is surprising, especially under the mild conditions employed and the refractory nature of cellulase enzyme.

The invention is further illustrated by the following examples.

The tests were conducted in the following equipment:

Laboratory Tumbler — The laboratory tumbler consisted of a 5 liter round bottom reaction flask which was indented. Connected to this flask by means of a reaction flask clamp was a tube of 370 mm. in length with the narrow part having an i.d. of 20 mm. and with a male 35/20 standard ball and socket piece attached to the narrow end. A Y-shaped glass tubing having a female 35/20 standard ball and socket piece on one leg and a silicon rubber septum on a second leg was attached to the tube by means of a clamp. The third leg of the Y-tube was connected to an aspirator. Located 120 mm. from the large end of the tube was a bearing. A second bearing was located 320 mm. from the large end. The entire apparatus fitted into a stand such that the two bearing were held in clamps and the apparatus held at a 30° angle below the horizontal. The Y-tube was held fixed by a clamp, thus allowing the tube and reaction flask to rotate at the ball and socket joint when the pulley was turned by a belt connected to a motor.

Plant Tumber — The plant tumbler was a double cone blender having a volume of 58 cu. ft., conical at both ends, and diverging from the axis about which the tumbler rotates. The tumbler was jacketed and cooling water or steam or a combination of both could be circulated through the jacket. The tumbler was rated at 15 lb. pressure or full vacuum. An oxide addition line passed through a steam line to vaporize the oxide, if necessary, and then through the axis into the tumbler. Material was introduced and removed through parts located at either of the conical ends and a vacuum line and pressure gauge were also located at one end.

The procedures used were as follows:

EXAMPLE 1

Laboratory Scale Process: 1000 g. samples of xanthan gum beer were adjusted to the desired pH, and the gum precipitated using 3 L. of isopropanol. The filtered gums were broken into coarse fibrous material, and treated with 10% (by dry weight) propylene oxide at 50° C. for 4 hours in te 3-necked flasked described above. The treated gums were dried and analyzed. Properties are shown in Table I.

EXAMPLE 2

50 g. samples of xanthan gum press cake containing about 50% solids and about 50% of water and isopropanol were treated with 5, 10, or 20% propylene oxide (by dry weight) for various times at various temperatures in the 3-necked flask described above. The treated gums were dried in an oven at 60° C., ad analyzed. Properties are shown in Table II.

EXAMPLE 3

Xanthan gum beer was adjusted to pH 5 with acid, and the gum was precipitated with 3 volumes of isopropanol. 1500 g. of the gum was "fluffed" in a mixer to comminute and break up the press cake. This gum contained about 50% solids and 50% water-isopropanol. The gum was placed in a mixer as described above, heated to either 50° or 70° C., and 8% by dry weight) propylene oxide introduced. The mixture was allowed to react 3 hours at 50° C., or 2 hours at 70° C. At the end of the reaction was evacuated, and te products dried at 60° C. in a steam oven. The properties are shown in Table III.

TABLE I

| Beer pH | 1% Product Vis., cps.[a] | pH | Salt Vis. cps.[b] | % Cellulase Vis. Loss[c] |
|---|---|---|---|---|
| 4 | 1564 | 6.3 | 1740 | 2.2 |
| 5 | 1558 | 6.5 | 1678 | 3.9 |
| 6 | 1454 | 6.8 | 1500 | 6.1 |
| 7 | 1496 | 7.0 | 1708 | 9.1 |
| 8 | 1490 | 7.2 | 1288 | 15.3 |

[a]Viscosity was determined in a Brookfield viscometer, 1% solution in distilled water, 60 rpm, No. 3 spindle, and 22° C.
[b]Viscosity was determined in a 1% NaCl solution.
[c]Cellulase activity was determined as follows:

Hydroxyethyl cellulase (HEC) is employed as te substrate for cellulase activity, as this material is available in pure form and is very susceptible to enzymatic degradation. Specifically, the HEC employed has a D.S. (degree of substitution) of 0.9–1.0 and a M.S. (molar substitution) of 1.8–2.0. The 2% viscosity in distilled water is 4,000–5,000 cps. at 25° C. as measured on a Brookfield Model LVT viscometer at 60 rpm. The trade name is Union Carbide HEC QP 4400.

The substrate solution is prepared by dissolving 20 gm. of HEC and 2gm. of preservative 1-(3-chloroallyl)-3,5,7-triaza-1-azonia-adamantane chloride in one liter of distilled water containing 16 ml. of 0.1N NaOh and 24 ml. of citrate buffer. The citrate buffer is prepared by dissolving 5.25 gm. of citric acid in 50 ml. of 1N NaOh and diluting this soluton to 250 ml.

The cellulase activity of a xanthan gum sample is determined by mixing 30 ml. of a 1% gum solution to 90 ml. of the HEC solution and incubating at 43°44° C. for 4 days. If, after 4 days, the viscosity of the solution decreases by less than 10%, the gum is considered cellulase negative. In general, untreated xanthan gum results in a decrease in viscosity of 90–97%.

EXAMPLE 4

A 50 gm. sample of a xanthan gum press cake containing about 50% solids and about 50% of water and isopropanol was treated with 10% propylene oxide (by dry weight) for 4 hours at 55° C. The treated gum was dried at 60° C. and milled. The 1% viscosity of the treated gum was 1030 cps while that of the untreated gum was 765 cps, an increase of 34.6 percent.

EXAMPLE 5

A 50 gm. sample of a xanthan gum press cake was treated with 10% propylene oxide (by dry weight) for 1 hour at 70° C. The treated gum was dried at 60° C. and milled. The 1% viscosity of the treated gum was 1200 cps, while that of the untreated gum was 785 cps, an increase of 52.9 percent.

EXAMPLE 6

Pivalolactone and glutraldehyde were employed as the cellulase inactivating agent. Both were employed at a 10% level based on dry gum weight and treatment at 70° C. for 1 hour. The other conditions were the samples as described above. In addition, B-propiolactone was employed at 6 and 10% levels (dry gum weight). Results are summarized in Table IV.

TABLE II

| Temp. ° C. | % PO | 1 Hour Vis. (cps) | pH | 2 Hour Vis. (cps) | pH | 3 Hour Vis. (cps) | pH | 4 Hour Vis. (cps) | pH |
|---|---|---|---|---|---|---|---|---|---|
| 55 | 0 | — | — | — | — | — | — | 754 | 8.1 |
| 55 | 10 | — | — | — | — | — | — | 1075 | 7.9 |
| 55 | 10 | — | — | — | — | 910 | 8.5 | — | — |
| 55 | 0 | — | — | — | — | — | — | 750 | 7.4 |
| 55 | 20 | — | — | — | — | — | — | 1050 | 8.5 |
| 55 | 20 | — | — | — | — | 1040 | 8.2 | — | — |
| 70 | 0 | — | — | — | — | 775 | 7.5 | — | — |
| 70 | 5 | — | — | — | — | 1210 | 8.2 | — | — |
| 70 | 0 | — | — | 754 | 8.1 | — | — | — | — |
| 70 | 10 | — | — | 1590 | 8.2 | — | — | — | — |
| *70 | 10 | — | — | 1260 | 7.8 | — | — | — | — |
| 70 | 10 | 1390 | 7.8 | — | — | — | — | — | — |
| *70 | 10 | 1150 | 7.6 | — | — | — | — | — | — |
| 70 | 0 | — | — | 785 | 7.1 | — | — | — | — |
| 70 | 20 | — | — | 1500 | 7.8 | — | — | — | — |
| *70 | 20 | — | — | 1450 | 7.8 | — | — | — | — |
| 70 | 20 | 1400 | 7.8 | — | — | — | — | — | — |
| *70 | 20 | 1200 | 7.7 | — | — | — | — | — | — |

*Tumbler reactor.

Viscosity was mesured using a Brookfield viscometer, at 1% solution in distilled water, 60 rpm, No. 3 spindle, at 22° C.

TABLE III

| Sample No. | Beer pH | 1% Product Vis., cps | KCl Vis., pH | KCl Vis., cps | % Cellulase Vis. Loss | Reaction Conditions |
| --- | --- | --- | --- | --- | --- | --- |
| Control | 5 | 660 | 6.1 | 1300 | 97.0 | — |
| 1 | 5 | 1100 | 6.2 | 1925 | 0 | 3 hr. at 50° C., 8% P.O. |
| 2 | 5 | 1000 | 6.3 | 1740 | 3.6 | 3 hr. at 50° C., 8% P.O. |
| 3 | 5 | 1150 | 6.1 | 1810 | 1.9 | 2 hr. at 70° C., 8% P.O. |
| 4 | 5 | 1210 | 6.1 | 1680 | 1.3 | 2 hr. at 70° C., 8% P.O. |

TABLE IV

| Sample No. | Oxide | 1% Product vis. cps | pH | KCl vis., cps | Celulase vis. loss |
| --- | --- | --- | --- | --- | --- |
| 1 | Glutaraldehyde | 1160 | 6.3 | 1580 | 1.9 |
| 2 | Pivalolactone | 4180 | 4.8 | 910 | +15.5 |
| 3 | 6% β-propiolactone | 1414 | 5.5 | — | 6.9 |
| 4 | 10% β-propiolactone | 1726 | 4.9 | — | 9.7 |

What is claimed is:

1. A process for inactivating cellulase enzyme in xanthan gum precipitated from a fermentation beer at a pH of from about 4 to about 8 comprising intermingling wet particulate chemically unmodified xanthan gum, having a solids content not above about 90% by weight, with 2-20% based on xanthan dry weight of an oxide reagent which is either propylene oxide, β-propiolactone, glutaraldehyde, pivalolactone, glycidol, epichlorohydrin or ethylene oxide at from about 40° to about 70° C., for from about 1 to about 5 hours, at ambient pressure and recovering the cellulase-inactivated xanthan gum thus produced.

2. The process of claim 1 wherein the temperature is from about 50° to about 70° C. and the amount of oxide reagent is from about 4–12% based on xanthan dry weight.

3. The process of claim 2 wherein the amount of oxide reagent is from about 8 to about 12% based on xanthan dry weight.

4. The process of claim 1 in which oxide reagent is propylene oxide.

5. The process of claim 1 in which the produced xanthan gum has a residual propylene oxide content of less than about 300 ppm.

6. The process of claim 1 in which the wet particulate xanthan gum contains 50–60% xanthan gum solids, the rest of the weight being water or water and isopropanol.

7. The product prepared by the process of claim 1.

8. The process of claim 1 in which the produced xanthan gum has a residual propylene oxide content of less than about 180 ppm.

9. A process according to claim 1 wherein the oxide reagent is propylene oxide, β-propiolactone, glutaraldehyde or pivalolactone.

* * * * *